United States Patent
Mehra et al.

(10) Patent No.: US 11,573,351 B2
(45) Date of Patent: Feb. 7, 2023

(54) OPTICAL SENSOR HAVING A MAGNETIC OPTICAL BARRIER

(71) Applicant: Apple Inc., Cupertino, CA (US)

(72) Inventors: Saahil Mehra, Saratoga, CA (US); Jacky G. Ko, Sunnyvale, CA (US); Saijin Liu, San Jose, CA (US)

(73) Assignee: Apple, Inc., Cupertino, CA (US)

( * ) Notice: Subject to any disclaimer, the term of this patent is extended or adjusted under 35 U.S.C. 154(b) by 391 days.

(21) Appl. No.: 16/812,152

(22) Filed: Mar. 6, 2020

(65) Prior Publication Data

US 2021/0278561 A1 Sep. 9, 2021

(51) Int. Cl.
| | |
|---|---|
| *H02J 7/00* | (2006.01) |
| *G01V 8/12* | (2006.01) |
| *G04G 21/02* | (2010.01) |
| *G04G 19/00* | (2006.01) |
| *H02J 50/10* | (2016.01) |
| *A61B 5/00* | (2006.01) |
| *H02J 7/02* | (2016.01) |
| *A61B 5/024* | (2006.01) |

(52) U.S. Cl.
CPC ............ *G01V 8/12* (2013.01); *A61B 5/02438* (2013.01); *A61B 5/681* (2013.01); *G04G 19/00* (2013.01); *G04G 21/025* (2013.01); *H02J 7/02* (2013.01); *H02J 50/10* (2016.02)

(58) Field of Classification Search
None
See application file for complete search history.

(56) References Cited

U.S. PATENT DOCUMENTS

| | | |
|---|---|---|
| 4,913,150 A | 4/1990 | Cheung et al. |
| 6,313,612 B1 * | 11/2001 | Honda .................. H02J 50/80 320/139 |
| 6,526,300 B1 | 2/2003 | Kiani et al. |
| 6,662,033 B2 | 12/2003 | Casciani et al. |
| 6,882,874 B2 | 4/2005 | Huiku |
| 7,206,621 B2 | 4/2007 | Aoyagi et al. |

(Continued)

FOREIGN PATENT DOCUMENTS

| | | |
|---|---|---|
| CN | 103876726 | 6/2014 |
| CN | 203943664 | 11/2014 |

(Continued)

OTHER PUBLICATIONS

U.S. Appl. No. 17/020,659, filed Sep. 14, 2020, Duan et al.
U.S. Appl. No. 17/473,745, filed Sep. 13, 2021, Liu et al.

*Primary Examiner* — Arun C Williams
(74) *Attorney, Agent, or Firm* — Brownstein Hyatt Farber Schreck, LLP

(57) ABSTRACT

An electronic watch includes a frame and a cover. The cover is attached to the frame, and the frame and cover at least partially define an interior volume of the electronic watch. An optical sensor assembly including a light emitter and a light receiver is positioned within the inter volume of the frame. An optical barrier is positioned between the optical sensor assembly and the cover and includes a magnetic material that forms a light blocking-wall between the light emitter and the light receiver. The magnetic material is configured to removably couple the electronic watch with a charging device via a magnetic attraction between the magnetic material and a magnetic component of the charging device.

20 Claims, 12 Drawing Sheets

(56) References Cited

U.S. PATENT DOCUMENTS

| | | |
|---|---|---|
| 8,463,345 B2 | 6/2013 | Kuhn et al. |
| 8,948,832 B2 | 2/2015 | Hong et al. |
| 9,226,663 B2 | 1/2016 | Fei |
| 9,558,336 B2 | 1/2017 | Lee |
| 9,597,014 B2 | 3/2017 | Venkatraman et al. |
| 9,743,838 B2 | 8/2017 | Richards |
| 9,763,607 B1 | 9/2017 | Acosta et al. |
| 9,861,286 B1 | 1/2018 | Islam |
| 10,032,557 B1 * | 7/2018 | Bossetti ............. H02J 7/025 |
| 10,092,197 B2 | 10/2018 | Han |
| 10,117,587 B2 | 11/2018 | Han |
| 10,178,959 B1 * | 1/2019 | Homyk ............. A61B 5/0261 |
| 10,181,021 B2 | 1/2019 | Verkatraman et al. |
| 10,188,330 B1 | 1/2019 | Kadlec et al. |
| 10,241,476 B1 * | 3/2019 | Moten ............... H02J 50/10 |
| 10,278,591 B2 | 5/2019 | Gil |
| 10,376,164 B2 | 8/2019 | Presura et al. |
| 10,417,513 B2 | 9/2019 | Lee |
| 10,433,739 B2 | 10/2019 | Weekly et al. |
| 10,444,067 B2 | 10/2019 | Hsu et al. |
| 10,485,437 B2 | 11/2019 | Wei et al. |
| 10,485,478 B1 * | 11/2019 | Mirov .............. A61B 5/14551 |
| 10,537,270 B2 | 1/2020 | Sarussi et al. |
| 10,586,525 B1 | 2/2020 | Wu et al. |
| 10,627,783 B2 * | 4/2020 | Rothkopf ........... A61B 5/0205 |
| 10,646,145 B2 | 5/2020 | Pekander et al. |
| 10,702,211 B2 | 7/2020 | Clavelle et al. |
| 10,760,955 B2 | 9/2020 | Chu et al. |
| 10,966,643 B1 * | 4/2021 | Vavadi ............... A61B 5/4845 |
| 11,018,524 B2 * | 5/2021 | Simpson ............. H04B 1/10 |
| 11,224,381 B2 | 1/2022 | McHale et al. |
| 2015/0054348 A1 * | 2/2015 | Akiya ................ H02J 7/025 |
| | | 307/104 |
| 2015/0099943 A1 | 4/2015 | Russell |
| 2016/0129279 A1 | 5/2016 | Ferolito |
| 2016/0278712 A1 | 9/2016 | Sagara |
| 2017/0095216 A1 | 4/2017 | Laty |
| 2017/0135633 A1 | 5/2017 | Connor |
| 2017/0172476 A1 | 6/2017 | Schilthuizen |
| 2017/0251963 A1 | 9/2017 | Hashimoto et al. |
| 2017/0315511 A1 | 11/2017 | Shim et al. |
| 2018/0085040 A1 | 3/2018 | Ferber et al. |
| 2018/0098708 A1 | 4/2018 | Lee |
| 2018/0344175 A1 | 12/2018 | Rulkov et al. |
| 2019/0072912 A1 | 3/2019 | Pandya et al. |
| 2019/0083034 A1 | 3/2019 | Shim et al. |
| 2019/0090766 A1 | 3/2019 | Block et al. |
| 2019/0090806 A1 | 3/2019 | Clavelle et al. |
| 2019/0167124 A1 | 6/2019 | Verkruijsse et al. |
| 2020/0163616 A1 | 5/2020 | Sakaya |
| 2021/0093237 A1 | 4/2021 | Venugopal et al. |

FOREIGN PATENT DOCUMENTS

| | | |
|---|---|---|
| CN | 109589095 | 4/2019 |
| CN | 109645972 | 4/2019 |
| EP | 3451117 | 3/2019 |
| KR | 20180042472 | 4/2018 |

* cited by examiner

OPTICAL SENSOR HAVING A MAGNETIC OPTICAL BARRIER

FIELD

The described embodiments relate generally to a wearable electronic device such as an electronic watch. More particularly, the described embodiments relate to devices and systems for coupling a charging unit to a watch or other electronic device.

BACKGROUND

A watch or other electronic device may include a housing that protects internal components of the device from moisture, dust, debris, or other contaminants. The device may contain various electronic components within the housing, such as one or more processors and components that provide or support a display, speaker, microphone, haptic feedback device, input devices (e.g., button and/or crown), electronic connectors, and so on. The device may also include a set of sensors for determining parameters of the device or a user, such as whether the watch is being worn, or a heart rate of the user. The set of sensors may include optical sensors, which in turn may include one or more light emitters for emitting light towards a user (e.g., toward the skin of a user), and one or more light receivers for detecting a reflected or scattered portion of the emitted light. Circuitry associated with the light emitters and receivers may generate electrical signals that are used to determine parameters of the device or the user (e.g., whether the watch is being worn, or the user's heart rate).

The device may also include a rechargeable battery that powers one or more of the components within the device, and a charging system for charging the battery. In some cases, the device may include a magnet that magnetically attracts the device to an external charger. The external charger may wirelessly couple with the charging system to charge the battery.

SUMMARY

Embodiments of the systems, devices, methods, and apparatus described in the present disclosure are directed to a watch or other electronic device (e.g., another type of wearable electronic device). The electronic components may include optical sensors that transmit light toward a user of the device and receive a reflected or scattered portion of that light to determine one or more parameters of the device or a user (e.g., is the user wearing the device, a heart rate of the user, and so on). The watch may include an optical barrier that isolates various light inputs and outputs from interfering with each other. The optical barrier may be or include a magnet that can be used to removably couple the watch with a charging device.

In a first aspect, the present disclosure describes an electronic watch. The watch may include a frame that at least partially defines an interior volume of the watch and a cover attached to the frame. The cover can further define the interior volume of the watch. The watch can include an optical sensor assembly positioned within the interior volume that includes a light emitter configured to emit light through the cover, and a light receiver configured to receive a reflected portion of the light through the cover. An optical barrier may be positioned between the optical sensor assembly and the cover. The optical barrier can include a magnetic material and form a light blocking wall between the light emitter and the light receiver. The magnetic material can be configured to removably couple the watch with a charging device via a magnetic attraction between the magnetic material and a magnetic component of the charging device.

In some embodiments, the optical barrier can define first and second apertures extending between top and bottom surfaces of the optical barrier. The first aperture can align with the light emitter and be configured to allow emitted light to pass from the light emitter and to the cover. The second aperture can align with the light receiver and be configured to allow the reflected portion of the light to pass from the cover to the light receiver. In some examples, the top surface of the optical barrier is mechanically coupled with the optical sensor assembly. The optical barrier can also be electrically grounded to the optical sensor assembly. The bottom surface of the optical barrier can be mechanically coupled with the cover. In some cases, the optical barrier is configured to shield the optical sensor assembly from electromagnetic interference. In further examples, the optical barrier can include a non-magnetic material.

In another aspect, the present disclosure describes an electronic device that includes a housing and a substrate positioned adjacent to a portion of the housing. The substrate can carry an optical transmitter positioned to emit light through the portion of the housing, and an optical receiver positioned to receive light through the portion of the housing. A light-blocking barrier may extend between the substrate and the housing and comprise a magnetic material.

In some embodiments, the light-blocking barrier can be configured to magnetically couple a charging device to the electronic device. The housing can also include a frame, and a cover attached to the frame. The portion of the housing, through which the optical transmitter emits and the optical receiver receives, can include a portion of the cover. In some examples, the light-blocking barrier defines an aperture extending between the substrate and the cover, where the aperture provides a light path between at least one of the optical transmitter or the optical receiver and the transparent cover. The cover can have a dome shaped structure defining an exterior surface. In some examples, the magnetic material can define a first portion of the light-blocking barrier, and the magnetic material can be surrounded by a non-magnetic material defining a second portion of the light-blocking barrier. The substrate can be mechanically coupled to the light-blocking barrier. In some cases, the light-blocking barrier at least partially shields the substrate from electromagnetic interference.

In another aspect, the present disclosure describes a wearable electronic device that includes a housing including a cover. The cover can include a first surface interior to the wearable electronic device, and a second surface exterior to the wearable electronic device. A light emitter can be coupled with the first surface and configured to emit light from the interior and through the cover of the wearable electronic device. A light sensor can be coupled with the first surface and configured to detect a portion of the emitted light received through the cover from the exterior of the wearable electronic device. A magnetic material can extend from the first surface and be configured to removably couple the wearable electronic device with a charging device at least partially based on a magnetic attraction.

In some embodiments, the magnetic material extends from the first surface to the second surface, and the magnetic material is integrated with the cover. The magnetic material can define an optical barrier between the light emitter and the light sensor. The magnetic material can define a first aperture extending between the light emitter and the cover, a second aperture extending between the light sensor and the cover, and the light barrier can be formed by a segment of the magnetic material positioned between the first and second apertures.

BRIEF DESCRIPTION OF THE DRAWINGS

The disclosure will be readily understood by the following detailed description in conjunction with the accompanying drawings, wherein like reference numerals designate like structural elements, and in which.

Figure 1A:
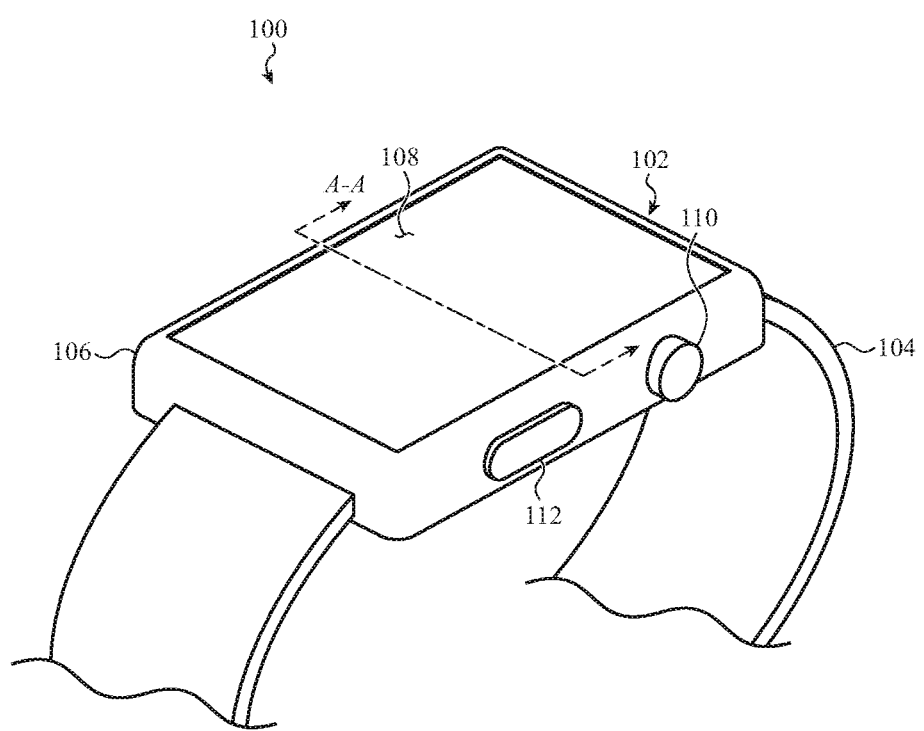
FIGS. 1A and 1B illustrate an example of a wearable device.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any characteristics attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

An electronic device such as a watch may have a sensor stack that can be used to detect one or more parameters associated with a user or the electronic device, such as a heart rate of the user; one or more parameters of the device, such as whether the device is being worn by a user; and so on. The sensor stack can include an optical sensor assembly which in turn can include light emitters that transmit light toward the skin of a user, and light receivers that detect a portion of the light that is reflected or scattered from the user's skin. A back cover of the device may include one or more transparent sections (e.g., sections that are transparent to at least a wavelength of light emitted by the device) that may define an outer portion of the device and partially contain the sensor stack within a housing of the device. In some embodiments, the device can include an optical barrier positioned between an optical sensor assembly and the cover. The optical barrier may be configured to reduce interference at or between different light sensors and/or emitters. Additionally, the device may include a battery for powering electrical components of the device. The battery may be charged using an internal charging system and an external charger. In some cases, it may be desirable to magnetically attach the charger to the device, such that the charger and the device can be easily coupled or decoupled. A magnet can be located within the device housing to magnetically couple the charger to the device. A problem, however, is that both the magnet and the optical barrier take up space within the device, which tends to increase the size (e.g., the height or thickness) of the device.

The following disclosure relates to devices and techniques for incorporating both a magnet and an optical barrier into an electronic device, or integrating both a magnet and an optical barrier into a sensor stack. The housing of the watch may include a frame, a back cover, and a front cover, which are coupled together to form an internal cavity of the device. The watch housing may contain various electrical components such as display components, one or more processors, a haptic engine, electronic components, sensor systems (e.g., input sensors, optical sensors, microphones, speakers), and so on. The sensor stack can interface with the skin of a user when the watch is worn by the user (i.e., the sensor stack can emit light toward the skin of the user, and receive light that reflects or scatters from the skin). Accordingly, the back cover may include one or more transparent components that allow light to exit and enter the watch housing (e.g., transparent components that may be visibly transparent or visibly opaque, but transmit light wavelengths emitted by the watch). In some cases, it may be desirable to seal the watch housing, for example, to protect internal components from dust, debris, moisture, or other contaminants. Further, sealing the watch housing can sometimes improve the accuracy of one or more electronic components, such as the optical sensor assembly. The sensor stack may be used to determine one or more parameters associated with the device or the user based on the transmitted and received light. These parameters can include, for example, a determination of whether the user is wearing the watch, or parameters pertaining to one or more physiological conditions such as the user's heart rate, blood oxygen saturation, and so on.

The watch housing may also contain a rechargeable battery for powering the electronic components, and a charging system for recharging the battery. The watch can include one or more structures for coupling the watch with a charging device, such as a magnetic optical barrier that can be used to magnetically couple a charging device with the watch for charging the battery.

The magnetic optical barrier can be positioned between the transparent cover and the optical sensor assembly to reduce undesirable interference between the light emitters and receivers. For example, the magnetic optical barrier can have a set of holes or apertures that align with respective ones of the light emitters or receivers. The apertures can provide light paths between the optical sensor assembly and the cover, so that emitted light is guided to travel through the cover and to the skin. For example, an aperture wall may block emitted light from traveling directly to a receiver, without first traveling through the transparent cover. A portion of light can reflect and/or scatter from the skin and travel back through the cover, through one or more apertures of the magnetic optical barrier, and to a receiver. The apertures can be defined by walls, which walls are in turn defined by the magnetic optical barrier. The aperture walls can also block light emitted from a first emitter from interfering with light emitted from other emitters of the optical sensor assembly.

The magnetic optical barrier can be used to magnetically couple a charging device to the watch. For example, a magnetic element or elements within the magnetic optical barrier can form a magnetic attractive force with one or more magnetic elements in a charging device. This magnetic attractive force can couple the watch with the charging device. For example, the magnetic attractive force may hold an outer surface of the watch against an outer surface of the charging device. In some cases, the respective magnets can be configured such that the magnetic attractive force is strong enough to support the weight of the watch or the charging device such that they remain coupled if one is supported and the other is left unsupported. At the same time, the respective magnets may also be configured such that a user can detach the watch from the charging device by pulling or otherwise physically separating the two components. Such magnetic coupling of the watch and charger may also be referred to as removably coupling the watch and the charging device. The watch and the charging device can also be configured such that, while they are magnetically coupled, the charging device charges the battery contained within the interior of the watch housing.

The magnetic optical barrier can be formed or otherwise manufactured and assembled to position the optical sensor assembly in relation to the cover. For example, light emitters and receivers may be aligned in a particular orientation in relation to the cover. In some examples, a first surface (e.g., bottom surface) of the magnetic optical barrier may couple with or abut an inside surface of the cover. The bottom surface of the magnetic optical barrier may be configured to contour to/match the profile of the inside surface of the cover, which may decrease interference between light sensors and receivers in the optical sensor assembly. Similarly, a second surface (e.g., top surface) of the magnetic optical barrier may be configured to couple with the optical sensor assembly. This may include the top surface being configured to contour/match the profile of the optical sensor assembly. In some examples, the magnetic optical barrier may have features that provide a defined orientation between the optical sensor assembly and the cover, for example, positioning light emitters and/or receivers of the optical sensor assembly to align with specific portions (e.g., light transmitting portions) of the cover. In some cases, this alignment may occur during manufacturing, which may include orienting and optomechanically coupling (e.g., adhesively bonding, welding, fusing, joining, and so on) the magnetic optical barrier with either or both of the cover or the optical sensor assembly.

The magnetic optical barrier may be formed from a single piece of magnetic material, or from multiple sections/portions of magnetic materials, or from an assembly of magnetic and non-magnetic components, or from a combination thereof. In some cases, the magnetic optical barrier may be molded, machined, or otherwise formed from a magnetic material using any suitable process. In some examples, this may include forming the magnetic optical barrier from a ferromagnetic material. In other examples, the magnetic optical barrier may be formed from a material that is magnetized at a later processing step, such as after it has been processed into a defined shape. In some embodiments, the magnetic optical barrier may be coated, undergo surface finishing, or otherwise be modified. For example, surface finishes on the magnetic optical barrier can be tuned to increase the sensor performance, and may include absorptive, scattering, or reflective surface finishes. In some cases, the surface (e.g., surface coating or surface finish) of the magnetic optical barrier may be configured to increase optical sensor performance, such as by increasing an optical signal, decreasing noise, decreasing interference, and so on.

In some embodiments, the magnetic optical barrier may include magnetic and non-magnetic components. For example, the magnetic optical barrier may include a central portion that is disk or otherwise-shaped, with a circular aperture through the center. An outer portion may include aperture walls configured to match the contour of the light emitters and receivers. The first portion of the magnetic optical barrier (e.g., central portion) may include a disk formed from magnetic material and the outer portion may be formed from a plastic, metal, ceramic, or other suitable material. In some cases, a multi-component magnetic optical barrier may reduce manufacturing cost or complexity, or achieve other desirable properties. In further examples, the magnetic optical barrier can include multiple discrete magnetic components. For example, an inner magnetic ring can form the magnetic optical barrier between various optical sensors and the sensor stack can further include an outer magnetic ring that defines an outer portion (e.g., edge or outer perimeter) of the sensor stack.

In some embodiments, the magnetic optical barrier may be integrated into the transparent cover. For example, the magnetic optical barrier can form one or more portions of the back cover. This may include co-forming the magnetic material with the transparent material to form the cover. The magnetic material may form one or more apertures as described herein, which may create light paths between the optical sensor assembly and the outer surface of the housing (e.g., outer surface of the back cover). In some cases, this can allow the optical sensor assembly to be positioned directly on an inner surface of the cover, which may reduce the thickness of the watch.

The techniques and embodiments described herein can in some cases decrease the size (e.g., height or thickness) of the device, for example, by enabling a reduction in layer count (e.g., a reduction in printed circuit board (PCB) layer count) or component count in the sensor stack and/or charging system, by integrating a magnetic coupling component with the optical barrier, and so on. The techniques and embodiments described herein can, in some cases, allow additional components to be incorporated into the device housing, or can free space for increasing the size of other components, such as the battery. The techniques and embodiments can additionally or alternatively decrease the size and/or amount of magnetic material needed for coupling a charging device, by moving the magnet closer to the outer surface of the device housing, and thus, closer to the charging device.

These and other embodiments are discussed below with reference to FIGS. 1-9. However, those skilled in the art will readily appreciate that the detailed description given herein with respect to these Figures is for explanatory purposes only and should not be construed as limiting.

FIG. 1A illustrates an example of a watch 100 that incorporates a magnetic optical barrier. The watch 100 may include a watch housing 102 and a watch band 104. Other devices that may incorporate a magnetic optical barrier include other wearable electronic devices, other timekeeping devices, other health monitoring or fitness devices, other portable computing devices, mobile phones (including smart phones), tablet computing devices, digital media devices, personal digital assistants, portable speaker devices, earbuds/headphones, camera devices, video recording devices (including wearable/mountable cameras), unmanned aerial vehicles, or the like.

The watch housing 102 may include a frame 106 that forms one or more sides of the housing 102, a front cover 108 that defines a front of the housing 102 that faces toward a user (i.e., away from a user's skin), and a back side (shown in FIG. 1B) that faces towards the user's skin when the watch is worn by the user. Alternatively, the housing 102 may include a singular housing member, or any number of two or more housing members that are joined together. The watch housing 102 may include metallic, plastic, ceramic, crystal, or other types of materials, or combinations of such materials.

The frame 106 may be a rigid structure that forms a sidewall of the watch housing 102. The frame 106 may also form part of a front or back surface of the housing 102 and mechanically couple with the front cover 108 (and display) and back cover to form an interior volume of the watch 100 which may contain electrical and other components of the watch 100 including the sensor stack described herein. The frame 106 may include at least one input device or selection device, such as a crown assembly, scroll wheel, knob, dial, button, or the like which may be operated by a user of the watch 100. For example, the frame 106 may include one or more openings for a crown 110 and/or button 112. The crown 110 may include a shaft that extends through the opening and interfaces with an internal crown assembly. The crown 110 may be manipulated by a user to rotate or translate the shaft, and the shaft may be mechanically, electrically, magnetically, and/or optically coupled to the internal crown assembly for example. A user's manipulation of the crown 110 may be used to manipulate or select various graphics displayed on the display, to adjust a volume of a speaker, to turn the watch 100 on or off, and so on. The button 112 may include a shaft or other structure that couples the button 112 with the housing 102. A user's manipulation of the button 112 may be used to manipulate, select, or initiate one or more functions of the watch 100. An internal portion of the frame may also include one or more features for mounting various components of the watch, such as electrical circuits/boards, a processor, battery, speaker components, input/output structures, haptic output devices, and so on.

The front cover 108 may be mounted on the front side of the watch housing 102 and may protect a display mounted within the housing 102. The display may be viewable by a user through the front cover 108, both of which may be part of a display stack that includes touch sensing and force sensing capabilities. The display may be configured to depict a graphical output, and a user may interact with the graphical output (e.g., using a finger or stylus). For example, a user may select or otherwise interact with a graphic, icon, or the like presented on the display by pressing or touching the display at the location of the graphic. The front cover 108 may form a part of or be attached to the frame 106. In some examples, the front cover 108 may include a crystal, such as a sapphire crystal or be formed of glass, plastic, or other materials.

The watch housing 102 may include structures for attaching the watch band 104 to the frame 106 and/or other portions of the housing 102 (such as the back cover). In some cases, the structures may include elongate recesses or apertures through which ends of the watch band 104 may be inserted and attached to the watch housing 102. In other cases (not shown), the structures may include indents such as dimples or depressions in the watch housing 102 that receive complementary features (e.g., compressible bumps, spring pins, and the like) that are attached to or threaded through ends of a watch band and used to secure the watch band 104 to the housing 102. The watch band 104 may be used to secure the watch 100 to a user, another device, a retaining mechanism, and so on.

In some embodiments, the watch 100 may include various combinations of the components described herein. That is, the watch 100 may lack the cover 108, the display, the crown 110, or the button 112. As one example, the watch 100 may exclude a digital electronic display (e.g., liquid crystal, light emitting diode, plasma, quantum dot, or the like), but include an audio input or output interface, a touch input interface, a haptic (force) input or output interface, or other input or output structures that do not require the display. When the watch 100 lacks the display, the front side of the watch 100 may include an opaque housing member or include one or more physical structures such as watch hands and a dial interface.

Figure 1B:
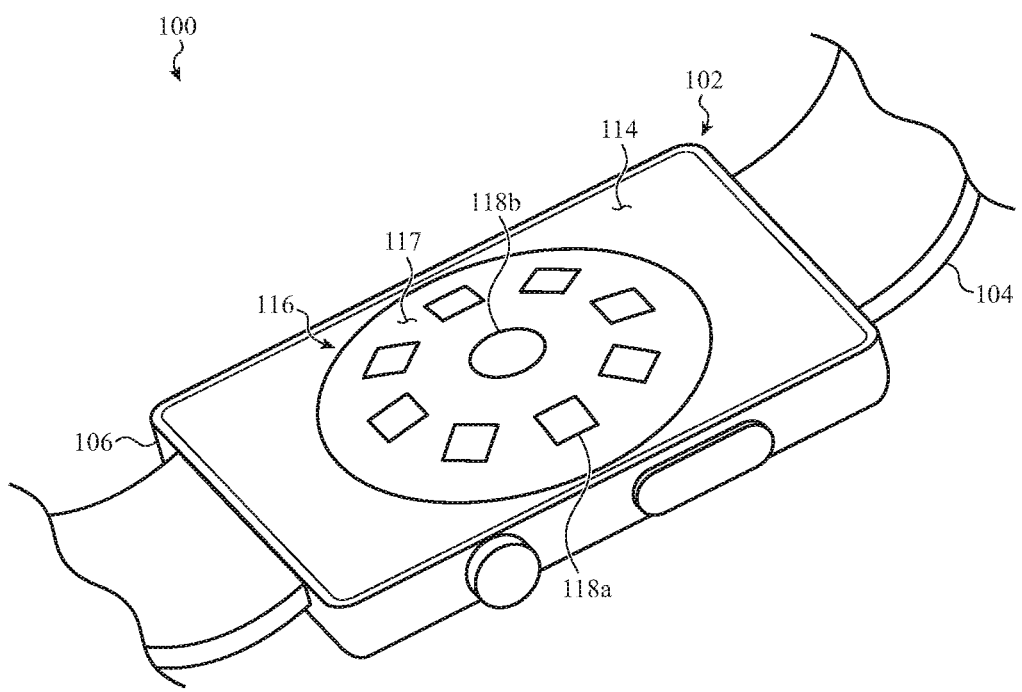

FIG. 1B illustrates an example of a back side of the watch 100 that includes a sensor stack and a magnetic optical barrier. The watch 100 may include a back member 114 and a cover 116 that is connected to the back member 114. In some embodiments, the back member 114 may be a distinct component that couples the cover 116 to the frame 106. In additional or alternative embodiments, the frame 106 may form a portion of the back side of the watch 100 and the cover 116 may be connected directly to the frame.

The cover 116 can be configured to contact or rest against the skin of a user, when the watch 100 is worn by the user. In some examples, the cover 116 can have a dome shaped exterior surface. The cover 116 can include one or more peripheral apertures 118. For example, the cover 116 can include a first portion 117 (non-transparent region) that limits or prevents light from traveling through the cover and the apertures 118, which allow light to travel through the cover 116. Some of the apertures 118 may provide a region through which light emitters (not shown in FIG. 1B) may emit light. For example, a first aperture 118a may provide a region through which a light emitter may emit light. The emitted light may travel into the tissue of the user and then may scatter, be absorbed, refracted, or reflected (hereinafter collectively referred to as reflected light) off of the skin, blood vessels, blood components, tendons, muscle, bones, or other tissue of the user. The reflected light from the user may pass back through one or more of the apertures 118 and be detected by light receivers (not shown in FIG. 1B) incorporated into the watch 100. For example, the light may pass through a second aperture 118b and to a light receiver positioned within the housing 102 of the watch 100. The apertures 118 may be defined by transparent sections that are surrounded by light blocking sections. For example, the first portion 117 may include masking sections around the apertures 118, which may include light blocking/filtering inks, coatings, or other light blocking elements adhered to or formed onto the cover 116. The first portion 117 may help prevent or reduce reflected light from entering other portions of the cover 116, which could cause interference with emitters, receivers, or other sensors positioned behind the cover 116. This may ensure acceptable measurement accuracy due to optical isolation of the reflected light.

In some examples, a charging system (not shown in FIG. 1B) for the watch 100 may be positioned behind the cover 116. The watch 100 may include a magnetic optical barrier for coupling an external charging device with the housing 102. In some embodiments, the external charging device may be placed, by a user, against the outer surface of the cover 116, and the magnetic optical barrier within the watch 100 (e.g., positioned behind the cover 116) may create an attractive force with a magnet in the external charging device. The magnetic attractive force between these components may secure the charging device to the housing 102, and an internal battery of the watch 100 may be charged.

Figure 2:
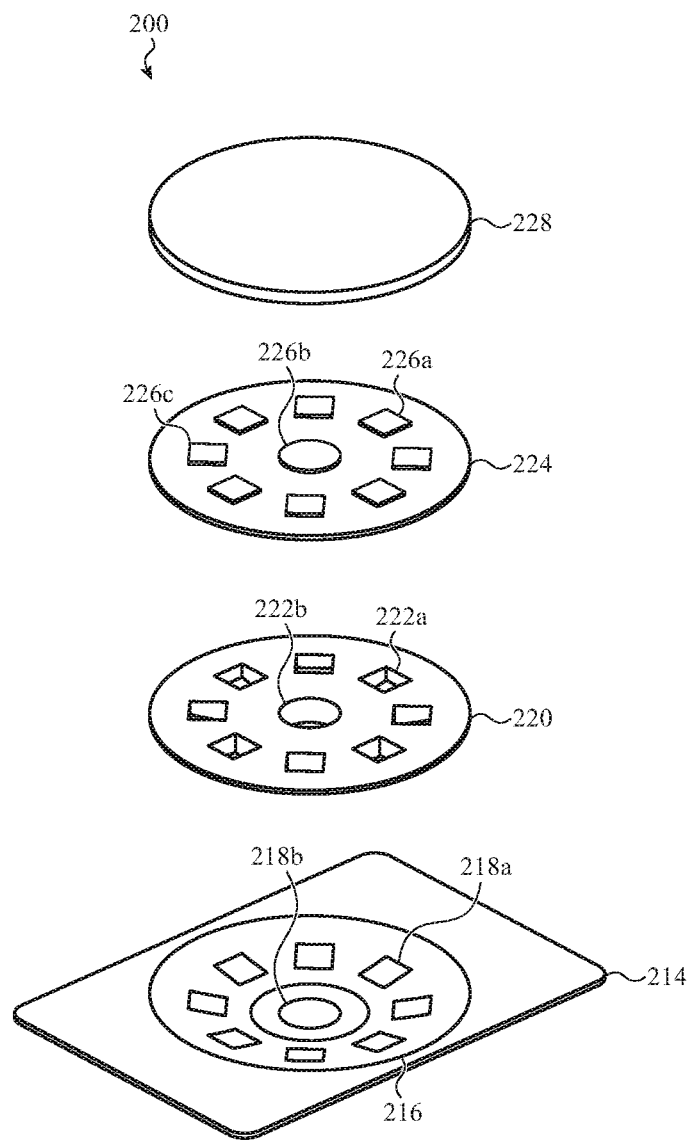
FIG. 2 illustrates an example exploded view of a sensor stack of a wearable device.

FIG. 2 illustrates an example exploded view of a sensor stack 200 of a wearable electronic device such as a watch. The sensor stack 200 can include a back member 214, which may be an example of the back member 114 described with reference to FIG. 1B; and a cover 216, which may be an example of the cover 116 described with reference to FIG. 1B. The sensor stack 200 can also include a magnetic optical barrier 220, an optical sensor assembly 224, and a circuit board 228 that supports operation of the sensor stack 200. The magnetic optical barrier 220 can be positioned between the cover 216 and the optical sensor assembly 224, and define apertures 222 that form light paths between the optical sensor assembly 224 and the cover 216. Such apertures 222 can help ensure that light emitted by the optical sensor assembly 224 travels in a desired path (e.g., to the skin of a user) before being reflected back toward the optical sensor assembly 224. Additionally or alternatively, the apertures 222 can reduce noise or interference between different light beams traveling along different light paths between the optical sensor assembly 224 and the user.

The optical sensor assembly 224 can include one or more optical units 226 arranged on a substrate such as a circuit board and configured to emit and receive light signals from the optical sensor assembly 224. Each optical unit 226 may include one or more light emitters (which may also be referred to as an optical transmitter), light receivers (which may also be referred to as an optical receiver), or a combination of light emitters and light receivers. In some embodiments, a first optical unit 226a can include a light emitter that emits light from the optical sensor assembly 224, and a second optical unit 226b can include a light receiver that detects light transmitted from outside the device and through the cover 216. In some embodiments, an optical unit 226 may include multiple light emitters, multiple light receivers, or various combinations of light emitters and light receivers. For example, the first optical unit 226a can include a light emitter that emits one or more predetermined wavelengths of light, and the second optical unit 226b can include multiple light receivers, where each receiver is configured to detect different wavelengths (or wavelength bands) of the portion of reflected light. In further examples, the optical units 226 may include multiple light emitters that emit light with different properties (e.g., wavelengths, intensities, modulation techniques, and so on). Still further, various light emitters can be configured to transmit light along different paths. For example, a first optics unit 226a may have a first light emitter that emits a first light beam at a first angle of incidence such that the reflected portion of the first light beam is detected at the second optics unit 226b. The first optics unit 226a can also include a second light emitter that emits a second light beam at a second angle of incidence such that a reflected portion of the second light beam is detected at a third optics unit 226c. These examples are provided to illustrate some of the possible configurations of the optical units. Accordingly, the optics units 226 can be configured with other combinations of light emitters and light receivers.

Generally, the sensor stack 200 can operate by emitting light from the first optics unit 226a. The light can travel through a first aperture 222a in the magnetic optical barrier 220 and towards a user, where the light can interact with tissue of the user. A portion of the light may be reflected from the user, travel through the cover 216, travel through a second aperture 222b in the magnetic optical barrier 220, and to the second optics unit 226b, where the light can impinge on one or more light receivers of the second optics unit 226b. The light receiver(s) may output an electrical signal in response to the received light. The electrical signal may indicate intensity, wavelength, phase, angle of impingement, or other property of the received light. The electrical signals output from the optical sensor may be transmitted to the circuit board where they can be processed, transmitted, filtered, amplified, digitized, stored, or otherwise used to determine one or more parameters associated with a user (e.g., is the user wearing the watch, a heart rate, blood-oxygen content, or the like).

The magnetic optical barrier 220, as described herein, may define one or more apertures 222 that form defined light paths between the optical sensor assembly 224 and the cover 216. For example, the magnetic optical barrier 220 may define apertures that extend between a first surface (top surface) of the magnetic optical barrier 220 and a second surface (e.g., bottom surface) of the magnetic optical barrier 220. In such embodiments, the apertures can each extend through the entire thickness of the magnetic optical barrier 220. The magnetic optical barrier 220 can be connected to the optical sensor assembly 224, which may include mechanically coupling (e.g., adhesively bonding, welding, press fitting, mechanical fastening, or the like) the magnetic optical barrier 220 to the optical sensor assembly 224 for example. The magnetic optical barrier 220 can be formed from a light blocking material, such that light emitted from the optical sensor assembly 224 can only reach the cover 216 (and skin of a user) by traveling through the apertures 222. Similarly, light reflected from a user (or other external light) may only reach the optics unit 226 through the apertures 222 defined by the magnetic optical barrier 220. In some embodiments, the walls of the apertures 222 may include light-blocking walls that reflect, refract, diffuse, absorb, or otherwise modify the light traveling through the apertures 222. In some embodiments, the magnetic optical barrier 220 or portions of the magnetic optical barrier 220 (e.g., walls of the apertures 222) may be coated, for example, with a light blocking, reflective, diffusive, absorbing, or other types of coatings.

The magnetic optical barrier 220 can be formed from or contain a magnetic material for coupling a charging device with an outside surface of the cover 216 and/or back member 214. In some embodiments, the magnetic optical barrier 220 is formed using a permanent magnet, examples of which may include ferritic material, ceramic materials, rare earth magnets, or the like. The magnetic material may be molded, machined, pressed, coated, combined with other materials, or processed in any other suitable manner to form the magnetic optical barrier 220. For example, the magnetic material may be processed to form a disk-shaped structure that defines the apertures 222, which can have a bottom surface that conforms to the inner surface of the cover 216 and a top surface that is configured to connect to the optical sensor assembly 224. The apertures 222 can extend between the bottom surface and the top surface of the magnetic optical barrier 220. This is just one example, and the magnetic optical barrier 220 may be processed into any suitable shape. In some embodiments, the magnetic optical barrier 220 could be configured as a temporary magnet such as an electromagnet. In such embodiments, the watch can be configured to determine when a charging device is in close proximity to the watch housing and activate the electromagnet to couple the charging device with the housing.

In some embodiments, the magnetic optical barrier 220 may be configured to reduce interference such as electromagnetic interference at one or more internal components of the watch. For example, the magnetic optical barrier 220 may be grounded to the optical sensor using a conductive adhesive, by soldering, or other electrical connector such as a via. The magnetic optical barrier 220 may also be coated or include materials that reduce interference (e.g., electromagnetic interference) at the optical sensor assembly 224, which could include configuring the magnetic optical barrier 220 to include an electrically insulating surface that contacts the inner surface of the cover 216.

The sensor stack 200 can be assembled in a variety of ways. In some embodiments, different layers (e.g., cover 216, magnetic optical barrier 220, optical sensor assembly 224, circuit board 228, and so on) can be connected to each other using one or more mechanical fastening techniques such as adhesive bonding, soldering, welding, fastening (e.g., press fit, rivets, etc.), and so on. For example, the magnetic optical barrier 220 may be connected to the cover 216 using a first adhesive and connected to the optical sensor assembly 224 using a second adhesive (e.g., electrically conductive adhesive, soldering, etc.). In some cases, the magnetic optical barrier 220 can be electrically grounded to the optical sensor assembly 224. The optical sensor assembly 224 can be connected to the circuit board 228 through soldering, mechanical fastener, and so on.

Figure 3:
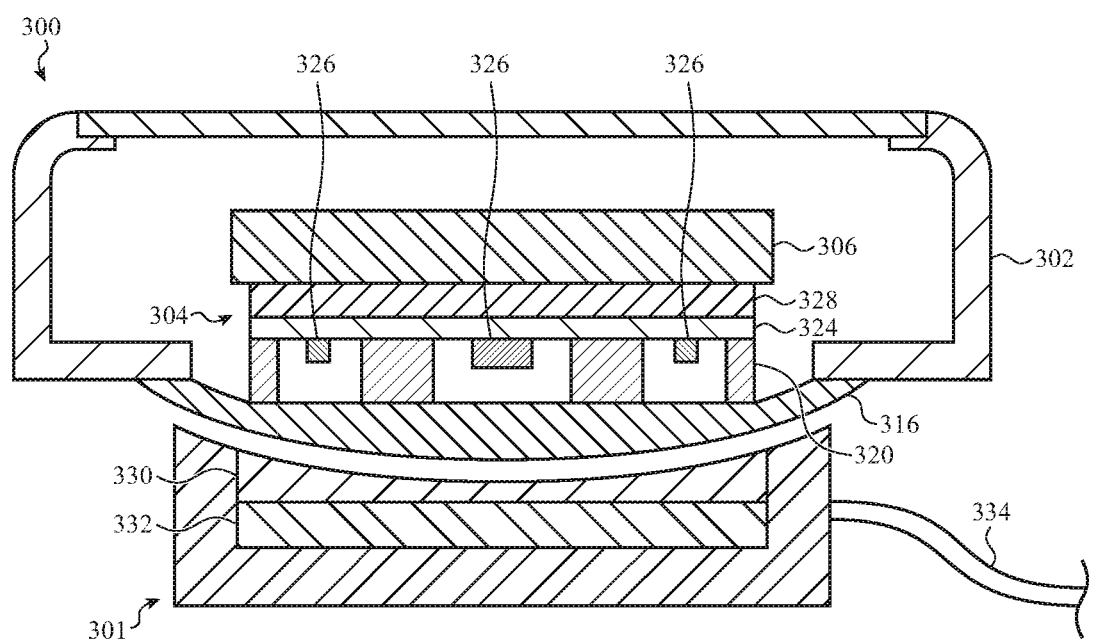
FIG. 3 illustrates an example cross-section of a sensor stack and charging system of a wearable device.

FIG. 3 illustrates an example cross-section of a watch 300 coupled with a charging device 301 taken along line A-A shown in FIG. 1A. The watch 300 may be an example of the watch 100 described with reference to FIGS. 1A-1B. The watch 300 may include a housing 302 that contains a sensor stack 304, which may be an example of the sensor stack 200 described with reference to FIG. 2; and a rechargeable battery system 306, which may include a rechargeable battery as described herein. The sensor stack 304 can include a magnetic optical barrier 320, an optical sensor assembly 324 including optics units 326, and a circuit board 328. The charging device 301 can include a magnetic coupler 330, a charging system 332 and a power cord 334.

Generally, the magnetic optical barrier 320 may include magnetic material, as described herein, and be configured to removably couple the charging device 301 to the watch 300. The charging device 301 may include a magnetic coupler 330, which may include permanent or temporary magnets as described herein and generate a magnetic attraction force with the magnetic optical barrier 320. In some embodiments, the charging device 301 may abut the cover 316, and may include a curved surface that interfaces with the outer surface of the cover 316 and is configured to position the charging device 301 in a defined orientation with respect to the watch 300. For example, the charging device 301 may include a curved outer surface that matches the curvature of the outer surface of the cover 316. Further, the magnetic coupler 330 may be positioned within the charging device 301 to facilitate positioning the charging device 301 and watch in a defined orientation (or range of orientations). That is, the outer curvature of the charging device 301 and configuration of the magnetic coupler 330 may bias the orientation of the charging device 301 relative to the cover 316.

The size (e.g., thickness, mass, outer dimensions, and so on) of the magnetic optical barrier 320 and magnetic coupler 330 may be configured to generate a magnetic force that removably couples a charging device 301 to an outer housing of the watch 300. For example, the magnetic force generated between the magnetic optical barrier 320 and the magnetic coupler 330 can be configured to support the weight of the charging device and additional forces that occur with movement of the watch (e.g., acceleration that occurs when the watch is picked up and moved to a new location). Accordingly, the magnetic force may be such that the charging device remains attached to the watch, when a watch is picked up and moved without physically supporting the charging device. The magnetic force between the magnetic optical barrier 320 and the charging device 301 can also be configured such that a user can physically separate the watch and the charging device.

The rechargeable battery system 306 and charging system 332 may be configured to wirelessly charge the battery of the watch when the charging device 301 is coupled with the watch 300. The rechargeable battery system 306 and charging device 301 may be configured to use electromagnetic inductive charging, radiative electromagnetic resonant charging, radio frequency wireless charging, or the like, or a combination thereof. The charging device 301 may include a power cord 334 which transfers power from a power source such as an electrical outlet to the charging system 332, which may be used to charge the rechargeable battery of the rechargeable battery system 306.

Figure 4:
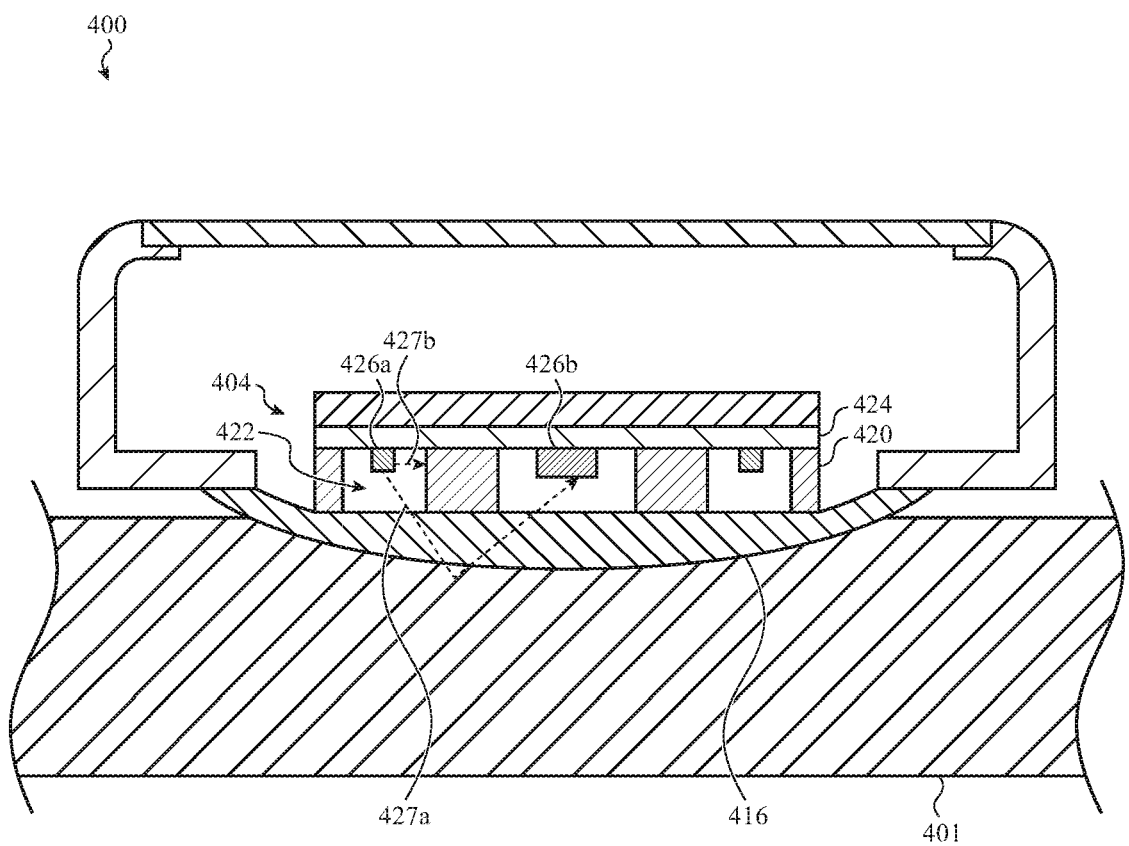
FIG. 4 illustrates an example cross-section of a sensor stack of a wearable device.

FIG. 4 illustrates an example cross-section of a watch 400 taken along line A-A shown in FIG. 1A positioned against a skin 401 of a user. The watch 400 can include a cover 416, which may be an example of the covers as described herein (e.g., covers 116, 216 and 316); and an optical sensor assembly 424, which may be an example of the optical sensors described herein (e.g., optical sensor assemblies 224 and 324). FIG. 4 provides an example of light paths 427 traveled by light emitted from a first optics unit 426a.

In the embodiment of FIG. 4, the first optics unit 426a includes a light emitter configured to emit light toward the cover 416, and a second optics unit 426b may include a light receiver configured to detect light that travels through the cover 416 from outside the watch 400. Light emitted from a first optics unit 426a may include a first beam that travels along a first light path 427a. The first beam may travel through an aperture 422 defined by walls of the magnetic optical barrier 420, through the cover 416 and interact with the skin 401 of a user. The portion of the first light beam may be reflected from the skin 401 and continue to travel along the first light path 427a, back through the cover 416, and impinge on the second optics unit 426b. The receiver of the second optics unit 426b may detect a portion of the first light and output an electrical signal indicative of one or more properties of the portion of the first light beam as described herein.

In some cases, light emitted from the first optics unit 426a can include a second light beam that travels along a second light path 427b. For example, the first optics unit 426a may include an emitter that emits light in multiple directions. The second light beam may travel along a path that is directed toward the second optics unit 426b. If the optical sensor system 404 did not include the magnetic optical barrier 420, then the second light beam would be received by the second optics unit 426b without having traveled to the skin 401 of the user. Such light may increase noise or lead to inaccurate measurements of the user. However, the second light beam intersects a light-blocking wall of the aperture 422 and is prevented from being directly transmitted to the second optics unit 426b. In some embodiments, the light-blocking walls of the aperture 422 may reflect the light beam (not shown), refract, diffuse, absorb, or otherwise modify the second light beam. In some embodiments, the light-blocking walls of the aperture 422 may be coated, or include surface features that modify the second light beam. For example, the light-blocking walls of the aperture 422 may be configured to reflect the second beam along a path that does not reach the second optics unit 426b.

In some embodiments, the magnetic optical barrier 420 and optical sensor assembly 424 may be configured to direct light along specific paths or at specific angles of incidence. The magnetic optical barrier 420 may define apertures 422 (e.g., depth, width, surface finish, shape, angle, etc.) that cause light emitted from the first optics unit 426a to travel along predefined paths, for example, along the first light path 427a. In some embodiments, the cover 416 (or portions of the cover) may include features that modify the light emitted from an optics unit 426. For example, the cover 416 could be shaped or coated to focus, scatter, refract, filter, or the like, the emitted light.

Figure 5A:
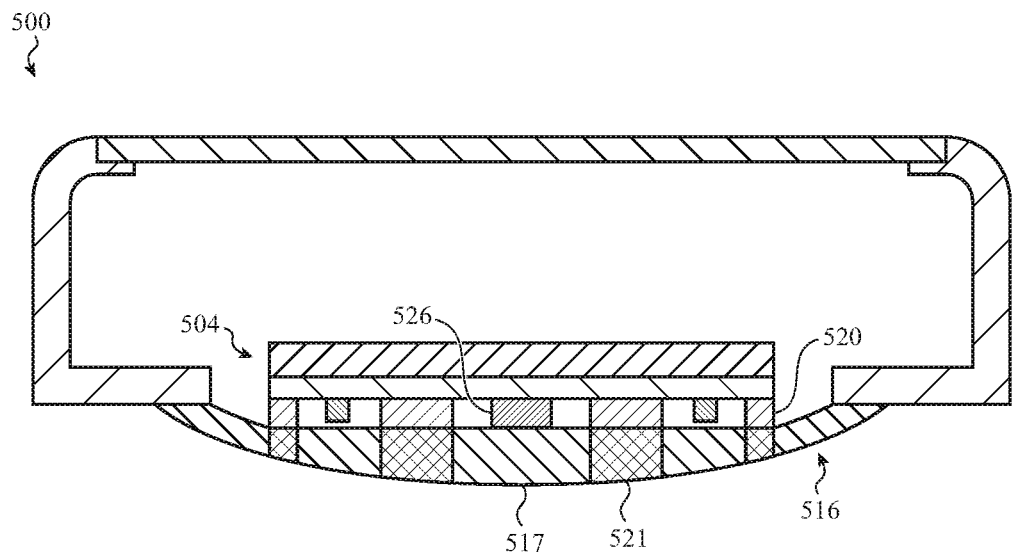
FIG. 5A illustrates an example cross-section of a sensor stack of a wearable device.

FIG. 5A illustrates an example cross-section of a watch 500 taken along line A-A shown in FIG. 1. The watch 500 may include a cover 516 that contains magnetic material or is co-formed with magnetic sections. The cover 516 can be an example of the covers described herein (e.g., covers 116, 216, 316, and 416), the magnetic optical barrier 520 can be an example of the magnetic optical barrier described herein (e.g., 220, 320, and 420), and the sensor stack 504 can be an example of the optical sensing assemblies as described herein (e.g., 200, 304, and 404).

In some embodiments, the cover 516 can be a multipart component that includes transparent sections 517 and magnetic material 521. The transparent sections 517 can allow light to pass into and out of the watch 500 and the magnetic material 521 can magnetically couple with a charging device as described herein. The magnetic material 521 can also create light-blocking sections within the cover 516. The transparent sections 517 and magnetic material 521 may be joined and/or formed such that the cover 516 defines a continuous outer surface. In some cases, the transparent section 517 and the magnetic material 521 may be joined and/or formed such that the cover 516 defines a continuous inner surface. The cover may be formed in a variety of ways that include one or more processes such as molding (e.g., co-molding, insert molding, or the like), machining, mechanically coupling (e.g., press fitting, adhesive boding, welding, sintering, or the like), or any other suitable technique.

In some embodiments, the sensor stack 504 can include a further optical barrier 520 positioned adjacent (abutting an inside surface of) the cover. In some cases, the optical barrier 520 may be magnetic, and in other cases, the optical barrier 520 may be non-magnetic or include a combination of magnetic and non-magnetic materials. In these examples, the magnetic material 521 may be used to couple a charging device to the watch 500 and the optical barrier 520 may function primarily to block/direct light as described herein. In other cases, the optical barrier 520 can be magnetic, as described herein, which can increase a magnetic attraction force between the charging device and the watch 500.

Figure 5B:
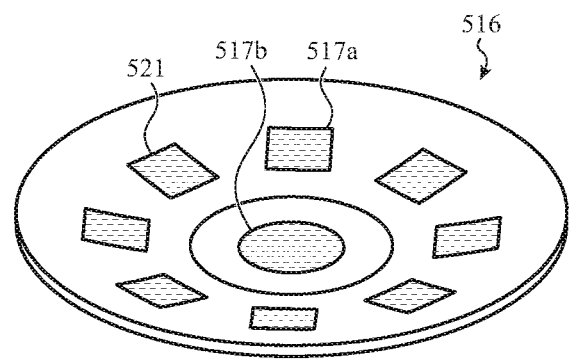
FIG. 5B illustrates an example view of a cover of the sensor stack shown in FIG. 5A.

As illustrated in FIG. 5B, the magnetic material 521 may form a curved disk shaped profile of the cover 516 and be joined with multiple transparent sections 517. The transparent sections 517 can align with the optics units 526 such that light emitted from the optics units can pass through these portions of the cover 516 and interact with a skin of a user, and travel back through the cover to one or more optics units 526.

Figure 6:
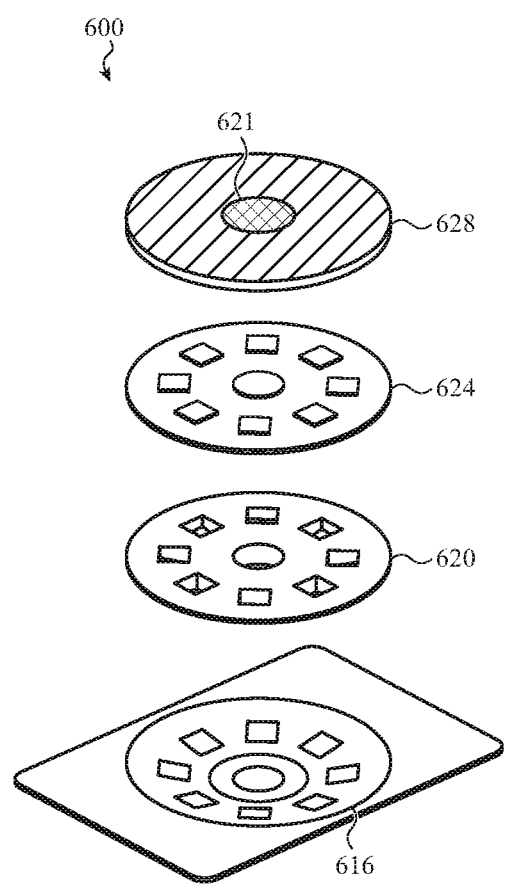
FIG. 6 illustrates an example exploded view of a sensor stack of a wearable device.

FIG. 6 illustrates an example exploded view of a sensor stack 600 of a wearable device. The sensor stack 600 may include a cover 616, a magnetic optical barrier 620, an optical sensor assembly 624, and a circuit board 628, as described herein. The sensor stack 600 can also include a second magnet 621. The second magnet 621 can be used, in addition to the magnetic optical barrier 620, to increase the coupling force between the wearable device and a charging device.

In some embodiments, the second magnet 621 can be positioned within a central portion of the circuit board 628. For example, the circuit board 628 can be configured with a central opening, and the second magnet 621 may be positioned within this opening and joined with the circuit board 628, the optical sensor assembly 624, or other components to secure the second magnet 621 within the wearable device. In some cases, the second magnet 621 may be positioned at other locations within the housing such as on top of the circuit board (forming another layer of the sensor stack 600), along an outer perimeter of the sensor stack 600, or the like.

Figure 7:
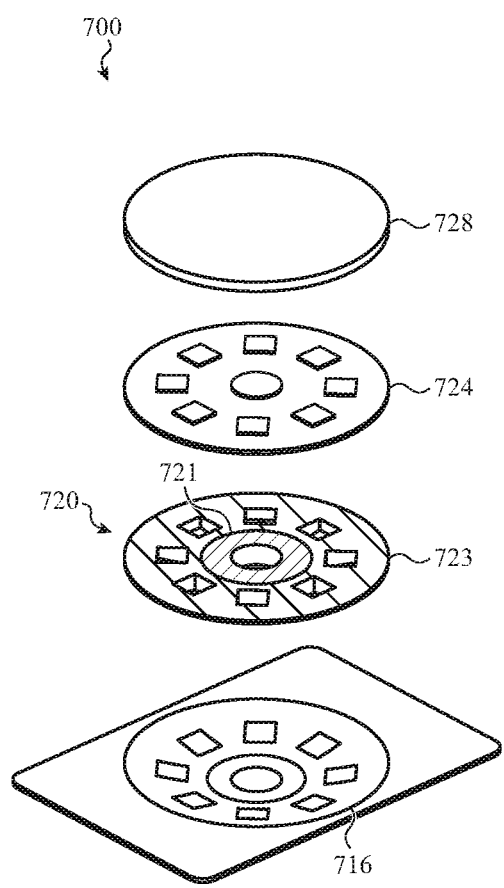
FIG. 7 illustrates an example exploded view of a sensor stack of a wearable device.

FIG. 7 illustrates an example exploded view of a sensor stack 700 of a wearable device. The sensor stack 700 may include a cover 716, a magnetic optical barrier 720, an optical sensor assembly 724, and a circuit board 728 as described herein. The example of FIG. 7 illustrates a multi-component magnetic optical barrier 720 that includes a magnetic material 721 and a non-magnetic material 723. For example, the magnetic material 721 can form an inner ring of the magnetic optical barrier 720 and be used to couple the electronic device with a charging device as described herein. The non-magnetic material 723 can form an outer section of the magnetic optical barrier 720, for example, a portion of the magnetic optical barrier 720 defining one or more peripheral apertures. A multi-component magnetic optical barrier 720 may reduce manufacturing complexity of the magnetic optical barrier 720, for example, by having the magnetic material 721 forming a less geometrically complex portion of the magnetic optical barrier 720.

Figure 8:
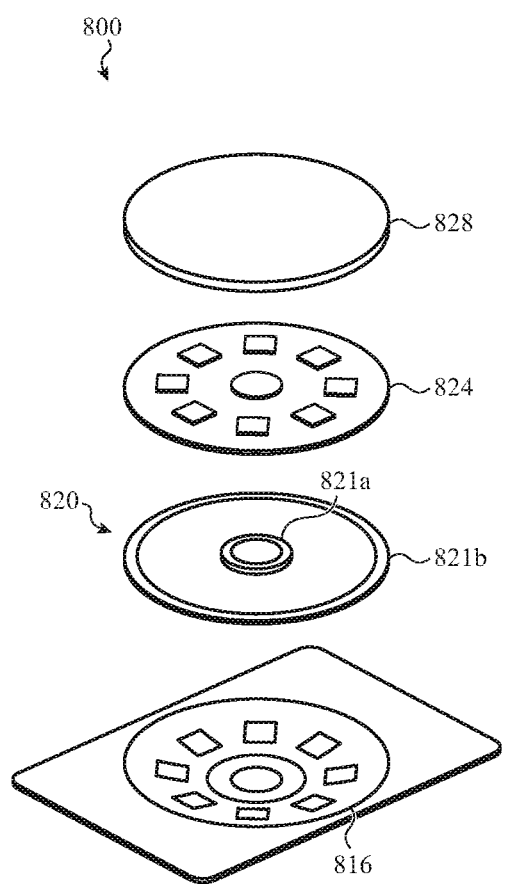
FIG. 8 illustrates an example exploded view of a sensor stack of a wearable device.

FIG. 8 illustrates an example exploded view of a sensor stack 800 of a wearable device. The sensor stack 800 may include a cover 816, a magnetic optical barrier 820, an optical sensor assembly 824, and a circuit board 828 as described herein. The example of FIG. 8 illustrates a multi-component optical barrier 820 that includes an inner magnetic optical barrier 821a and an outer component 821b, which can be magnetic or non-magnetic. For example, the inner magnetic optical barrier 821a can isolate one or more central optics units from one or more peripheral optics units located on the optical sensor assembly 824. The inner magnetic optical barrier 821a can be used to couple the electronic device with a charging device as described herein. The outer component 821b can form an outer portion of the magnetic optical barrier 820, which may define an outer perimeter or edge of the magnetic optical barrier 820. In some cases, the outer component 821*b* may be magnetic and used to couple the electronic device with a charging device as described herein. In other cases, the outer component 821*b* may be nonmagnetic. In further examples, the magnetic optical barrier 820 can be configured with more or fewer magnetic components that are configured to isolate one or more regions or optics units located on the sensor assembly 824, or more or fewer (or no) nonmagnetic components.

Figure 9:
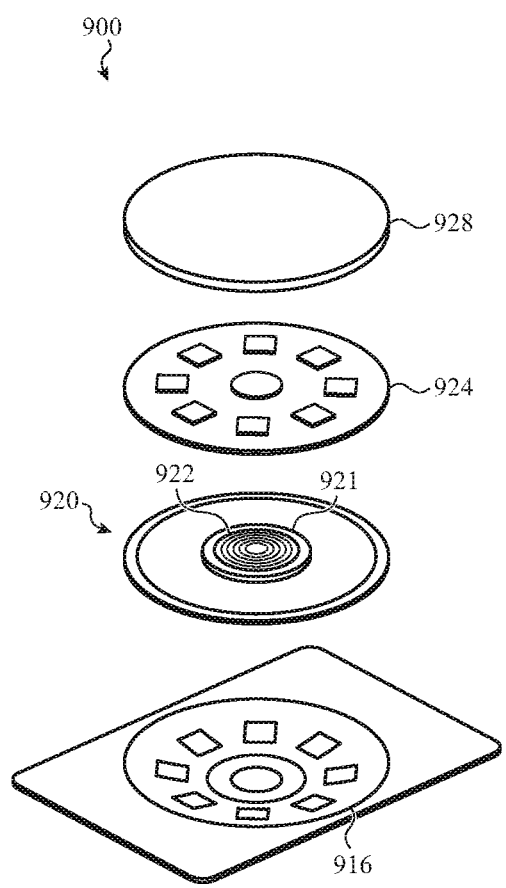
FIG. 9 illustrates an example exploded view of a sensor stack of a wearable device.

FIG. 9 illustrates an example exploded view of a sensor stack 900 of a wearable device. The sensor stack 900 may include a cover 916, a magnetic optical barrier 920, an optical sensor assembly 924, and a circuit board 928 as described herein. The example of FIG. 9 illustrates embodiments that include optical components 922 such as lenses, filters, and the like co-integrated with a magnetic component 921 to form the magnetic optical barrier 920. For example, the magnetic component 921 may define one or more apertures in the magnetic optical barrier 920, as described herein. In some examples, an optical component 922 such as a lens (e.g., Fresnel lens), collimator, filter, or the like can be positioned within one or more of those apertures. Accordingly, light passing through the apertures defined by the magnetic optical barrier 920 may be modified and/or redirected by the optical component 922 positioned within the aperture. For example, a lens could be used to focus light traveling from outside the electronic device on one or more light receivers located on optical sensor assembly 924. In other examples, the optical components 922 can split, filter, collimate, or otherwise modify light traveling through (e.g., entering or exiting) one or more apertures of the magnetic optical barrier 920. In some cases, a first aperture (e.g., defined by the magnetic component 921) may include a first optical component 922 such as a Fresnel lens, and a second aperture defined by another portion of the magnetic optical barrier 920 (not shown) may include a second optical component 922 such as a light filter.

The optical component(s) 922 can be co-integrated with the magnetic component 921 in a variety of ways. In some cases, the optical component 922 can be mounted within an aperture defined by the magnetic component 921 by operations such as press fitting, encapsulating, over molding, adhesive bonding, and so on. In this regard, the optical component 922 may be coupled to the magnetic component 921 such that light passing through the aperture also passes through the optical component.

Figure 10:
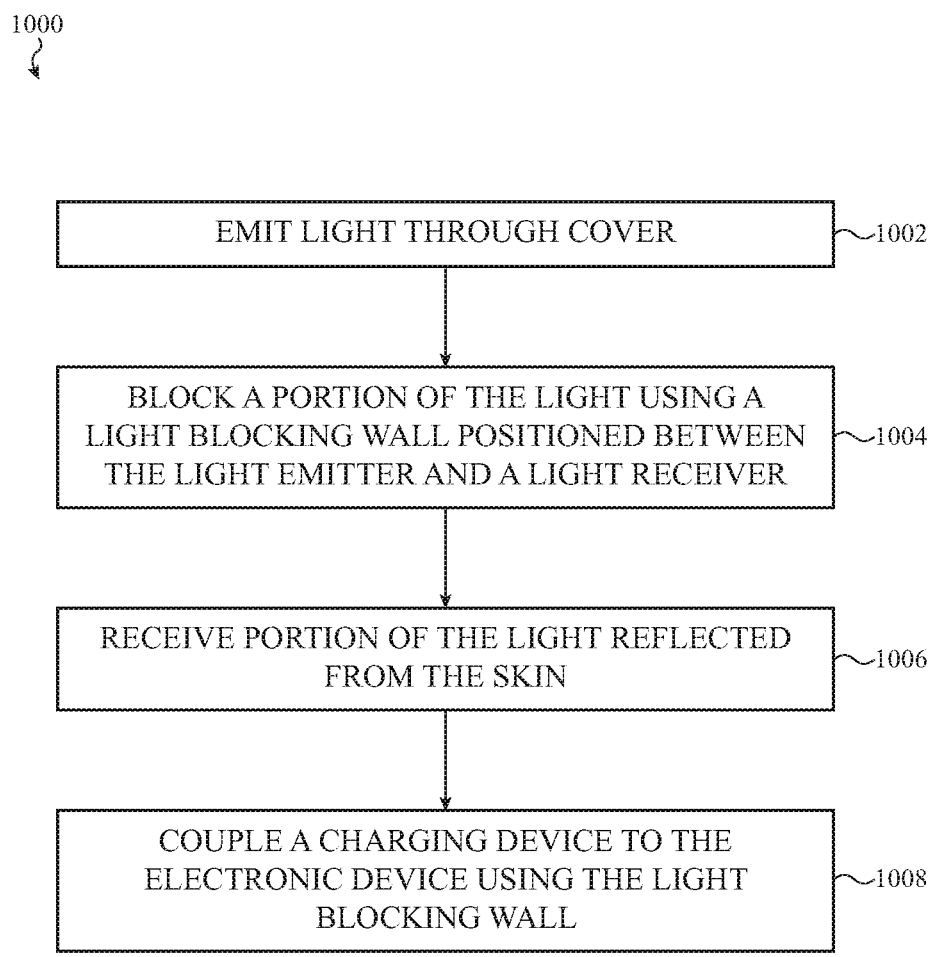
FIG. 10 illustrates an example method of using a magnetic optical barrier positioned within a wearable device.

FIG. 10 illustrates an example method 1000 of using a wearable device that includes a magnetic optical barrier. The method 1000 may be performed using the devices, systems, and apparatus described herein, such as a watch having a sensor stack that includes a cover, a magnetic optical barrier, and an optical sensor, as described herein.

At 1002, the wearable device may emit light from a sensor stack and through the cover of the wearable device. In some examples, the emitted light may travel through an aperture defined by a magnetic optical barrier that is positioned between the optical system and the cover. The device may emit a single wavelength of light, a band of wavelengths, broad spectrum light, or a combination thereof. The light may travel into the skin of a user and interact with tissue of the user such as skin tissue, muscle, blood vessels, blood, and so on. For example, different tissues may absorb specific wavelengths of light, thereby decreasing an intensity of those wavelengths. A portion of the light that interacted with the skin may be reflected back toward the wearable device.

At 1004, the magnetic optical barrier can block a portion of the emitted or reflected light. For example, apertures defined by the magnetic optical barrier may block or prevent light at defined angles of incidence from traveling to other components within the sensor stack or other components of the wearable device. In this regard, walls defined by the magnetic optical barrier may form the apertures and function to direct light in a desired direction (e.g., toward a skin of a user).

At 1006, a portion of the light that interacted with the skin may be reflected from the skin, travel back through the cover of the wearable device, through an aperture in the magnetic optical barrier, and to the optical sensor. A receiver on the optical sensor may detect the reflected portion of light and output an electrical signal indicative of one or more properties of the detected light. For example, the electrical signal may indicate an intensity of one or more wavelengths of the detected light.

At 1008, the wearable device may need to be charged. For example, a rechargeable battery contained within the housing of the wearable device may be low on power or out of power. A charging device may be positioned adjacent to the cover (or other portion of the housing) and a magnetic force between a magnet of the magnetic optical barrier and a magnet within the charging device can temporarily secure the charging device to the electronic device. The rechargeable battery may be wirelessly charged by the charging device.

Figure 11:
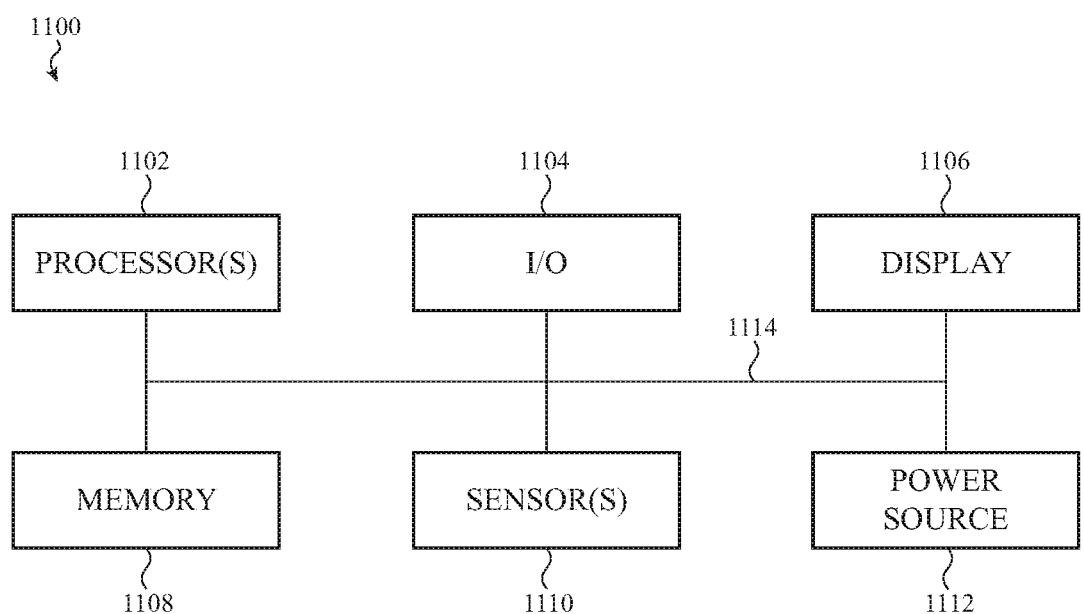
FIG. 11 illustrates an example electrical block diagram of an electronic device such as a watch or other suitable electronic device.

FIG. 11 illustrates an example electrical block diagram of an electronic device 1100, which may in some cases take the form of any of the watches or other wearable electronic devices as described with reference to FIGS. 1A-8. The electronic device can include a processor 1102, an input/output (I/O) mechanism 1104 (e.g., an input/output device, such as a touch screen, crown or button, input/output port, or haptic interface), a display 1106 (e.g., a light emitting display), memory 1108, sensors 1110 (e.g., an optical sensing system), and a power source 1112 (e.g., a rechargeable battery). The processor 1102 can control some of all of the operations of the electronic device 1100. The processor 1102 can communicate, either directly or indirectly, with some or all of the components of the electronic device 1100. For example, a system bus or other communication mechanism 1114 can provide communication between the processor 1102, the I/O mechanism 1104, the display 1106, the memory 1108, the sensors 1110, and the power source 1112.

The processor 1102 can be implemented as any electronic device capable of processing, receiving, or transmitting data or instructions. For example, the processor 1102 can be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitable computing element or elements.

It should be noted that the components of the electronic device 1100 can be controlled by multiple processors. For example, select components of the electronic device 1100 (e.g., a sensor 1110) may be controlled by a first processor and other components of the electronic device 1100 (e.g., the display 1106 may be controlled by a second processor, where the first and second processors may or may not be in communication with each other.

The I/O mechanism 1104 can transmit and/or receive data from a user or another electronic device. An I/O device can include a display, a touch sensing input surface, one or more buttons (e.g., a graphical user interface "home" button), one or more cameras, one or more microphones or speakers, one or more ports, such as a microphone port, and/or a keyboard. Additionally or alternatively, an I/O device or port can transmit electronic signals via a communications network, such as a wireless and/or wired network connection. Examples of wireless and wired network connections include, but are not limited to, cellular, Wi-Fi, Bluetooth, IR, and Ethernet connections.

The memory 1108 can store electronic data that can be used by the electronic device 1100. For example, the memory 1108 can store electrical data or content such as, for example, audio and video files, documents and applications, device settings and user preferences, timing signals, control signals, and data structures or databases. The memory 1108 can be configured as any type of memory. By way of example only, the memory 1108 can be implemented as random access memory, read-only memory, Flash memory, removable memory, other types of storage elements, or combinations of such devices.

The electronic device 1100 may also include one or more sensors 1110 positioned almost anywhere on the electronic device 1100. The sensor(s) 1110 can be configured to sense one or more type of parameters, such as but not limited to, pressure, light, touch, heat, movement, relative motion, biometric data (e.g., biological parameters), and so on. For example, the sensor(s) 1110 may include a heat sensor, a position sensor, a light or optical sensor, an accelerometer, a pressure transducer, a gyroscope, a magnetometer, a health monitoring sensor, and so on. Additionally, the one or more sensors 1110 can utilize any suitable sensing technology, including, but not limited to, capacitive, ultrasonic, resistive, optical, ultrasound, piezoelectric, and thermal sensing technology.

The power source 1112 can be implemented with any device capable of providing energy to the electronic device 1100. For example, the power source 1112 may be one or more batteries or rechargeable batteries. Additionally or alternatively, the power source 1112 can be a power connector or power cord that connects the electronic device 1100 to another power source, such as a wall outlet.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. An electronic watch, comprising:
    a frame at least partially defining an interior volume of the electronic watch;
    a cover attached to the frame and further defining the interior volume;
    an optical sensor assembly positioned within the interior volume and comprising:
        a light emitter configured to emit light through the cover; and
        a light receiver configured to receive a reflected portion of the light through the cover; and
    an optical barrier positioned between the optical sensor assembly and the cover, the optical barrier comprising a magnetic material and forming a light-blocking wall between the light emitter and the light receiver, wherein;
    the magnetic material is configured to removably couple the electronic watch with a charging device via a magnetic attraction between the magnetic material and a magnetic component of the charging device.

2. The electronic watch of claim 1, wherein the optical barrier defines first and second apertures extending between top and bottom surfaces of the optical barrier.

3. The electronic watch of claim 2, wherein:
    the first aperture aligns with the light emitter and is configured to allow emitted light to pass from the light emitter to the cover; and
    the second aperture aligns with the light receiver and is configured to allow the reflected portion of the light to pass from the cover to the light receiver.

4. The electronic watch of claim 2, wherein the top surface is mechanically coupled with the optical sensor assembly.

5. The electronic watch of claim 4, wherein the optical barrier is electrically grounded to the optical sensor assembly.

6. The electronic watch of claim 2, wherein the bottom surface is mechanically coupled with the cover.

7. The electronic watch of claim 1, wherein the optical barrier is configured to shield the optical sensor assembly from electromagnetic interference.

8. The electronic watch of claim 1, wherein the optical barrier further comprises a non-magnetic material.

9. An electronic device, comprising:
    a housing;
    a substrate positioned adjacent to a portion of the housing and carrying,
        an optical transmitter positioned to emit light through the portion of the housing; and
        an optical receiver positioned to receive light through the portion of the housing; and
    a light-blocking barrier extending between the substrate and the housing and comprising a magnetic material.

10. The electronic device of claim 9, wherein the light-blocking barrier is configured to magnetically couple a charging device to the electronic device.

11. The electronic device of claim 9, wherein:
    the housing comprises:
        a frame; and
        a cover attached to the frame; and
    the portion of the housing comprises a portion of the cover.

12. The electronic device of claim 11, wherein the light-blocking barrier defines an aperture extending between the substrate and the cover, the aperture providing a light path between at least one of the optical transmitter or the optical receiver and the cover.

13. The electronic device of claim 11, wherein the cover has a dome-shaped exterior surface.

14. The electronic device of claim 9, wherein;
    the magnetic material defines a first portion of the light-blocking barrier; and
    the magnetic material is surrounded by a non-magnetic material defining a second portion of the light-blocking barrier.

15. The electronic device of claim 9, wherein the substrate is mechanically coupled to the light-blocking barrier.

16. The electronic device of claim 15, wherein the light-blocking barrier at least partially shields the substrate from electromagnetic interference.

17. A wearable electronic device, comprising:
a housing including a cover, the cover comprising:
- a first surface interior to the wearable electronic device; and
- a second surface exterior to the wearable electronic device;

a light emitter coupled with the first surface and configured to emit light from the interior and through the cover of the wearable electronic device;

a light sensor coupled with the first surface and configured to detect a portion of the emitted light received through the cover from the exterior of the wearable electronic device; and a magnetic material extending from the first surface and configured to removably couple the wearable electronic device with a charging device at least partially based on a magnetic attraction.

18. The wearable electronic device of claim 17, wherein:
the magnetic material extends from the first surface to the second surface; and
the magnetic material is integrated with the cover.

19. The wearable electronic device of claim 17, wherein the magnetic material defines an optical barrier between the light emitter and the light sensor.

20. The wearable electronic device of claim 19, wherein:
the magnetic material defines a first aperture extending between the light emitter and the cover and a second aperture extending between the light sensor and the cover; and
the optical barrier is formed by a segment of the magnetic material positioned between the first and second apertures.

* * * * *